United States Patent [19]

Brumbach

[11] Patent Number: 5,562,609
[45] Date of Patent: Oct. 8, 1996

[54] ULTRASONIC SURGICAL PROBE

[75] Inventor: Joseph F. Brumbach, Niles, Ill.

[73] Assignee: FibraSonics, Inc., Chicago, Ill.

[21] Appl. No.: 319,677

[22] Filed: Oct. 7, 1994

[51] Int. Cl.⁶ ................................. A61B 17/20
[52] U.S. Cl. ................. 604/22; 604/35; 604/272; 606/169; 606/170; 607/97
[58] Field of Search ................. 128/200.16, 763; 433/119; 604/22, 35, 36, 43, 44, 156, 264, 266, 268, 272, 274; 606/167, 169, 170, 171, 185, 189; 607/97; 601/2

[56] References Cited

U.S. PATENT DOCUMENTS

| | | |
|---|---|---|
| 2,227,727 | 1/1941 | Leggiadro . |
| 3,542,031 | 11/1970 | Taylor . |
| 3,589,363 | 6/1971 | Banko . |
| 3,732,858 | 5/1973 | Banko . |
| 3,805,787 | 4/1974 | Banko . |
| 3,823,717 | 7/1974 | Pohlman et al. ............ 604/22 X |
| 3,844,272 | 10/1974 | Banko . |
| 3,896,811 | 7/1975 | Storz . |
| 3,930,505 | 1/1976 | Wallach . |
| 3,990,452 | 11/1976 | Murry et al. . |
| 3,996,935 | 12/1976 | Banko . |
| 4,061,146 | 12/1977 | Baehr et al. . |
| 4,493,694 | 1/1985 | Wuchinich ............... 604/22 |
| 4,516,398 | 5/1985 | Wuchinich . |
| 4,660,573 | 4/1987 | Brumbach . |
| 4,689,040 | 8/1987 | Thompson ............... 604/22 |
| 4,921,476 | 5/1990 | Wuchinich . |
| 5,151,083 | 9/1992 | Pichler ................... 604/22 |
| 5,178,605 | 1/1993 | Imonti ................... 604/22 |
| 5,248,297 | 9/1993 | Takase ................... 604/22 |
| 5,254,082 | 10/1993 | Takase . |
| 5,286,256 | 2/1994 | Mackool ................. 604/22 |
| 5,391,144 | 2/1995 | Sakurai et al. ............ 604/22 |

Primary Examiner—Corrine M. McDermott
Assistant Examiner—N. Kent Gring
Attorney, Agent, or Firm—Welsh & Katz, Ltd.

[57] ABSTRACT

A hollow operating needle for an ultrasonic surgical probe for fragmenting and removing material from the body has an elongated tapered portion which is coupled at its larger end portion to an ultrasonic motor for receiving and transmitting vibrations along the length of the needle to the operating end of the needle, with the needle defining a plurality of spaced apart openings extending from the operating tip end terminating at a distance substantially less than the distance to the larger end portion, whereby a substantial portion of irrigating fluid supplied adjacent the operating end portion of the needle reaches the operating tip end of the needle and the surgical site and another substantial portion of the fluid passes through the plurality of openings without reaching the operating tip of the needle. A generally concentrically positioned sleeve can be positioned about the needle extending from a housing enclosing the ultrasonic motor, thereby forming an annular passage with the needle through which irrigating fluid can be passed and can exit the annular passage adjacent the operating tip end portion of the needle.

13 Claims, 2 Drawing Sheets

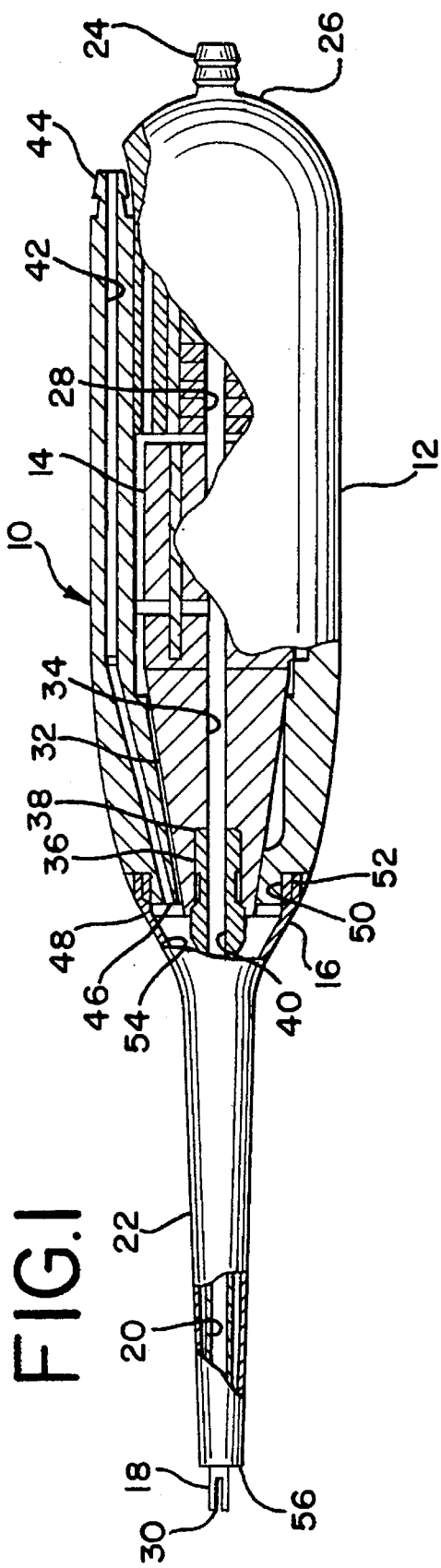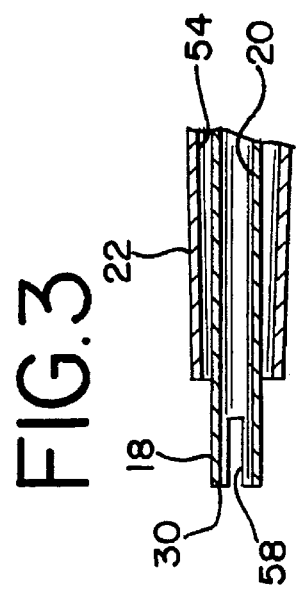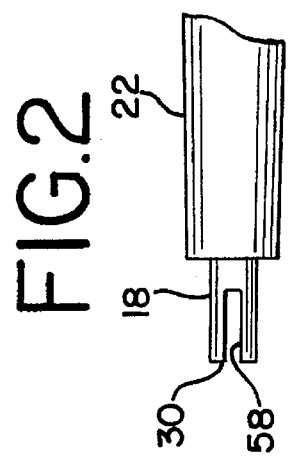

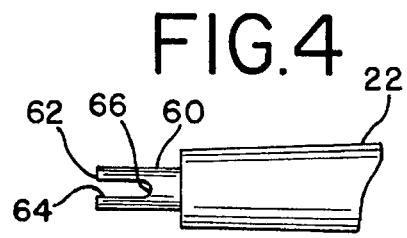
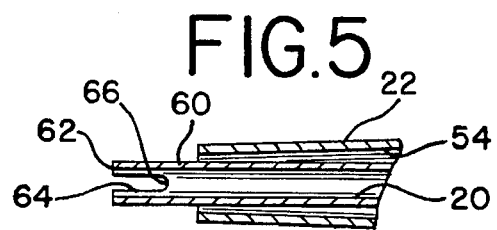
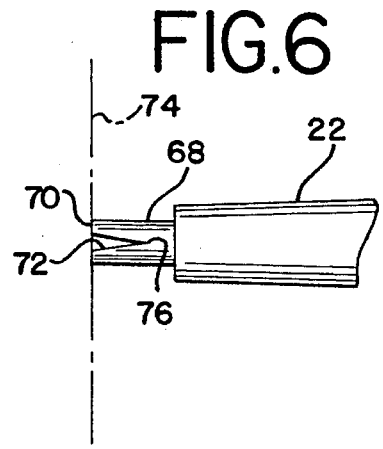
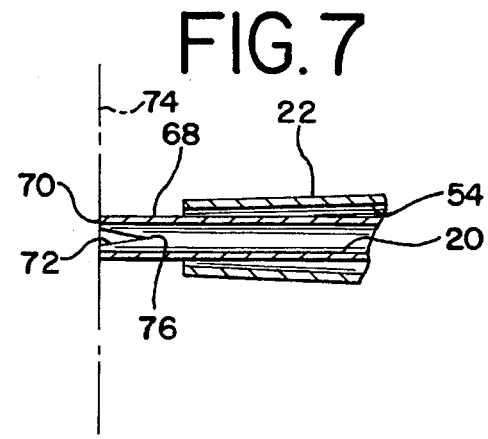
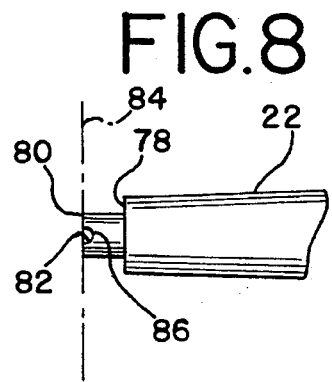
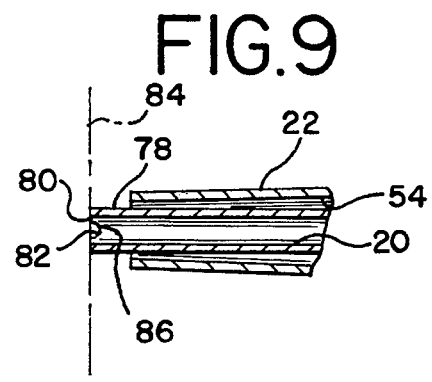
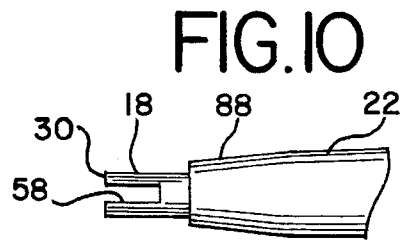
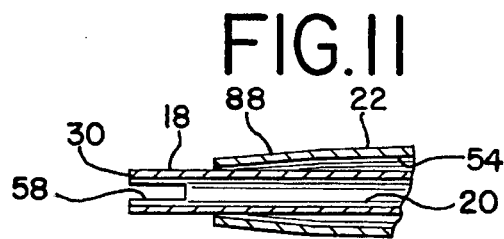

5,562,609

ULTRASONIC SURGICAL PROBE

BACKGROUND OF THE INVENTION

1. Field of the Invention

The present invention relates to ultrasonic surgical probes or scalpels for use in the removal of inorganic or organic tissue from a living body, and, more particularly, to an ultrasonic surgical tool or needle capable of imparting ultrasonic vibrations to tissue and calculi in a living body, such as a tumor, cataract or stone, to fragment the tissue or calculi, and of removing fragmented tissue, calculi and fluids from the surgical site.

2. Description of Related Art

Ultrasonic probes or scalpels for the fragmentation and removal of inorganic materials and fluids from living beings are known to the art. For example, U.S. Pat. No. 2,227,727, issued Jan. 7, 1941 to Vincent Leggiardro, discloses an apparatus for fragmenting naturally formed stones, such as bladder stones, kidney stones, and the like, utilizing a high speed reciprocating rod which may have a blunt end, a sharp or chisel point end, a cutting blade, or combinations thereof, such as a cutting blade having a blunt end.

While the apparatus disclosed in U.S. Pat. No. 2,227,727 involved a two part housing, with the sonic transducer in one part and the reciprocating rod in another part, in later apparatus the transducer and probe were connected together to form a unitary instrument. In U.S. Pat. No. 3,896,811, issued Jul. 29, 1975 to Karl Storz, the transducer and rod-like probe are coupled and both are enveloped by a jacket providing an air gap and preventing the sides of the probe from contacting the body except at its end. Furthermore, the probe may have a scalloped end to effect the dissolution or break-up of stones.

An improvement in such instruments is disclosed in U.S. Pat. No. 3,990,452, issued Nov. 9, 1976 to Edward J. Murry and Joseph F. Brumbach, which also reviews a number of articles relating to the development of ultrasonics in medicine and, particularly for use in cataract surgery, and notes the incorporation of irrigation and aspiration with ultrasonics.

A particular arrangement in an ultrasonically vibrated surgical tool using an irrigation fluid and an anti-coagulant, is disclosed in U.S. Pat. No. 4,493,694, issued Jan. 15, 1985 to David G. Wuchinich, utilizes a hollow tool having a suction passage and at least one pre-aspirating orifice in the wall of the tool, and a sleeve concentrically spaced about the tool for admitting fluid from a supply into the space between the sleeve and the tool and passing substantially all of the fluid through the pre-aspirating orifice.

Although the arrangement of having substantially all of the fluid pass through the pre-aspirating orifice, as in U.S. Pat. No. 4,493,694, may be useful in some operations, it is often preferable to have a substantial portion of the irrigating fluid flow to or spray the surgical site to assist in washing the fragmented material or tissue and any excess blood from the site into the end of the tool assisted by suction. In the arrangement where a substantial portion of the irrigating fluid desirably flows to or is sprayed on the surgical site, an anticoagulant is not employed as such an additive may cause excessive bleeding at the site. In one commercial ultrasonic probe, a shorter sleeve is employed, such that the open end of the sleeve does not cover the pre-aspiration orifice, and no anticoagulant is used, and thereby the surgical site is irrigated to assist the removal of material from the site without causing excessive bleeding due to an anticoagulant.

However, none of these arrangements are completely satisfactory, particularly where the volume of irrigation and other conditions of operation of the tool varies as selected by the surgeon and with the surgical procedure. Therefore, there is a need for an improved ultrasonic surgical tool construction which provides for improved fragmentation of tissue and calculi, and which can provide for a consistent, substantial flow of irrigation fluid at the operating end of the tool under various operating parameters, while providing improved operation of the tool.

SUMMARY OF THE INVENTION

Hence, it is one object of the present invention to provide an improved needle for an ultrasonic surgical probe.

It is another object of the present invention to provide an improved needle for an ultrasonic surgical probe wherein a means is provided for consistently assuring a substantial portion of the fluid supplied to the probe will be applied to the surgical site which assurance is not dependent on the amount of fluid and suction supplied to the probe.

It is still another object of the present invention to provide an improved needle for an ultrasonic surgical probe having means for consistently assuring a substantial portion of the fluid supplied to the probe will be applied to the surgical site and a portion of the fluid is provided to the suction path of the probe without reaching the surgical site.

These and other objects and advantages of the present invention will be apparent from the following description considered in conjunction with the accompanying drawings.

In accordance with the present invention an improved ultrasonic surgical probe for fragmenting and removing material from the body is provided having a handpiece containing an ultrasonic motor capable of generating ultrasonic vibrations, and a hollow operating needle extending outwardly from the handpiece having an operating end portion defining a plurality of spaced apart tip end openings extending from the operating end of the needle toward the handpiece, the needle coupled to the motor to receive and transmit ultrasonic vibrations therefrom along the length of the needle. Optionally, a sleeve can be positioned about the needle extending from the handpiece toward, but less than the full distance to the operating end of the needle. The sleeve, if used, and the needle define an open ended annular space for the passage of fluid supplied to the handpiece through the annular space. The handpiece further includes means for connecting the hollow operating needle to a source of suction such that suction can be applied to cause material to be drawn into the end of the needle and to pass through the hollow portion of the needle. The handpiece may also include means for connecting the handpiece to a source of fluid, particularly where a sleeve as noted above is used, such that fluid can flow through the annular space between the operating needle and the sleeve and exit from the open end of the annular space.

The improved needle of this invention, during its operation with ultrasonic vibrations being generated by the motor in the handpiece and transmitted to the operating end of the needle, with suction applied to the hollow portion to the needle to draw material therethrough and with a sleeve as described above and with fluid supplied to the annular space defined by the sleeve and the needle, results in a substantial portion of the fluid exiting the annular open end of the sleeve reaching the operating end of the needle and hence the surgical site, and another substantial portion of the fluid passing through the plurality of tip end openings defined in the needle for passage through the hollow needle without reaching the operating end of the needle and the surgical site. In this manner the surgical site is irrigated by a substantial portion of the fluid supplied to the handpiece to irrigate the site and to assist the flow of the fluid, blood and tissue or other matter separated from the tumor or calculi or other mass of the patient's body by the operating end of the needle of the probe into the end of the needle and the hollow passage therein and through the handpiece to means for collecting the material. Further in this manner, another substantial portion of fluid supplied to the handpiece passes through the plurality of tip end openings in the needle to cool the needle and ultrasonic motor and to maintain the suction and the flow of material removed from the surgical site through the needle and handpiece in the event the end of the needle is obstructed such as by being temporarily pushed against the tumor or other mass.

In accordance with this invention, the plurality of spaced apart tip end openings in the operating needle may be generally rectangular and may extend axially from the operating end of the handpiece. The plurality of tip end openings preferably comprises two openings or may comprise three or more openings, limited only by the strength and/or integrity of the needle material, which is preferably titanium or an alloy of titanium defining the needle tip portion. The plurality of tip end openings in the needle operating end portion may include other shapes, for example a modification of a rectangular opening, namely by having its closed end toward the handpiece being semicircular in shape, as being formed by a radius; or triangular or curvilinear, particularly arcuate, with the apexes thereof extending toward the handpiece and the transverse plane formed by the bases thereof defining the tip of the operating end of the needle.

Unexpectedly, it has been found that through the use of the needle of the present invention considerably more material can be removed from test tissue-masses as compared to probes under the same operating conditions using pre-aspirating orifices as heretofore described. It has further been unexpectedly found that a wider range of tissue can be fragmented and removed than could be fragmented and removed with the heretofore described probes having pre-aspirating orifices in the needle of the probe spaced from the tip end.

BRIEF DESCRIPTION OF THE DRAWINGS

FIG. 1 is a side view, partially in cross-section, showing schematically, an ultrasonic surgical probe of the present invention.

FIG. 2 is an enlarged view of a portion of FIG. 1 showing details of one embodiment of the present invention.

FIG. 3 is enlarged sectional view of the embodiment of the invention as shown in FIG. 2.

FIG. 4 is a view identical to FIG. 2 of a modification of the embodiment of the invention as shown in FIGS. 1–3.

FIG. 5 is a view identical to FIG. 3 showing the modification illustrated in FIG. 4.

FIG. 6 is a view identical to FIG. 2 showing another embodiment of the invention.

FIG. 7 is a view identical to FIG. 3 showing the embodiment of the invention illustrated in FIG. 6.

FIG. 8 is a view identical to FIG. 2 showing still another embodiment of the invention.

FIG. 9 is a view identical to FIG. 3 showing the embodiment of the invention illustrated in FIG. 8.

FIG. 10 is a view identical to FIG. 2 showing another embodiment similar to the embodiment of FIGS. 1–3.

FIG. 11 is a view identical to FIG. 3 showing the embodiment illustrated in FIG. 10.

DESCRIPTION OF THE PREFERRED EMBODIMENTS

In the preferred embodiments of the needle and ultrasonic surgical probe of the present invention, which are schematically illustrated in FIG. 1, the probe is generally referenced by numeral 10. A handpiece housing 12, which preferably is of non-conducting material, such as a polymer, encloses an ultrasonic motor 14. Extending outwardly from one end 16 of housing 12 is an operating needle 18 having an axial bore 20. In the preferred embodiments a sleeve 22 is generally concentrically positioned about and spaced from needle 18. Sleeve 22 may be a single molded piece as shown, or may comprise two or more sections glued or otherwise secured together, with the several sections of polymers of different properties, e.g. one part relatively rigid and another part relatively flexible. A power source (not shown) is connected to ultrasonic motor 14, which may be a known type of ultrasonic motor, such as an ultrasonic transducer with piezoelectric crystals or a magneto-strictive transducer which may be electromagnetically excited, but preferably is the former. Power can be applied to motor 14 through electrical conductors led through suitable openings (not shown) in housing 12.

In the preferred embodiments, housing 12 further includes a nipple 24 at its rear end 26 opposite end 16 supporting needle 18 and sleeve 22, to which is connected a suction or aspiration source (not shown). Extending generally axially through housing 12 and ultrasonic motor 14 is a suction or aspiration passage 28 which is coupled to nipple 24 and to bore 20 of needle 18 so that upon suction applied at nipple 24 is applied through passage 28 and bore 20 to the operating end 30 of needle 18. Housing 12, in the embodiments illustrated in FIG. 1, also encloses a motor 14 and horn 32 which is coupled to needle 18 and which is capable of transmitting ultrasonic vibrations from motor 14 to needle 18. Horn 32 has an axial hollow bore 34, which constitutes a portion of suction passage 28. Horn 32 at its end has an axial recess 36 which is internally threaded. The end 38 of the operating needle 18 opposite its operating end 30 is enlarged and externally threaded so as to be securely but releasably threadedly mounted in the recess 36 of horn 32. End 38 of needle 18 further includes a bore 40 which is coaxial with bore 20 of the needle and permits suction applied through passage 28 to be applied therethrough.

In the preferred embodiments where a sleeve 22 as defined herein is used, housing 12 further includes an irrigating fluid passage 42 formed therein, and a nipple 44 located near rear end 26 to which a supply of fluid (not shown) can be connected. Irrigating passage 42 extends to end 16 and exits housing 12 at port 46. Sleeve 22 has a flared end portion 48 having internal threads 50 in the substantially cylindrical end portion thereof which engage external threads 52 on end 16 of housing 12 so as to be securely, but releasably threadedly mounted to housing 12. When sleeve 22 is securely mounted on housing 12, irrigation passage 42 is in communication with annular space 54 between sleeve 22 and needle 18 through port 46 to permit fluid supplied to nipple 44 to flow through passage 42, port 46 and annular space 54 to the open end 56 of sleeve 22.

In the preferred embodiment shown schematically in FIG. 1, and more particularly in FIGS. 2 and 3, needle 18 in its portion extending rearwardly from end 30, includes a plurality of spaced apart tip end openings, which in the embodiment shown, is a pair of spaced apart generally rectangular longitudinally directed slits or slots 58. Although a pair of slots 58 is shown, a larger number of slots can be employed, for example three or four, providing the end 30 of needle 18 remains intact during use. Although the preferred needle material is titanium or an alloy of titanium, and is not considered brittle even with the transmission of ultrasonic vibrations during the operation of the probe, a larger number of slots may permit the breaking off of small pieces during extreme conditions of longer use than would be encountered in expected surgical procedures.

Another preferred embodiment of the present invention is illustrated in FIGS. 4 and 5, which is schematically generally shown in FIG. 1, and wherein components which are common to the first described preferred embodiments have the same reference numerals as in FIGS. 1–3. In this embodiment, needle 60 in the portion thereof extending axially from its operating end 62 toward housing 12, has a pair of slots 64 which are generally rectangular, as in the embodiment shown in FIGS. 2 and 3, but the ends 66 are rounded or arcuate, thus eliminating the internal corners of the slots 58 in the earlier described embodiment.

In the preferred embodiment shown in FIGS. 6 and 7, and also schematically in FIG. 1 and having common elements therewith in the drawings having the same reference numerals, needle 68, in the portion thereof extending axially from its operating end 70 toward housing 12, has a pair of spaced apart openings 72 which are substantially triangular in shape. Openings 72 in needle 68 have their bases and the operating end portions of the needle therebetween forming a plane 74 which is transverse to the axis of needle 68 which defines the tip of needle 68, and the apexes 76 of the substantially triangular shaped openings 72 extend toward housing 12. As in the case of needles 18 and 60 having generally spaced apart tip end openings 58 and 64 in the form of generally rectangular slots, a larger number of openings 72 in needle 68 may be employed as may be limited by the integrity of the material of the needle.

Another preferred embodiment is illustrated in FIGS. 8 and 9, and also schematically shown in FIG. 1 with common elements bearing the same reference numerals. In this embodiment, the portion of needle 78 extending axially from the operating end 80 thereof toward housing 12 has a pair of curvilinear shaped spaced apart tip end openings 82. Openings 82 may be substantially arcuate in shape, and may comprise more than two openings, for example three or four. Openings 82 in needle 78 have their bases and the operating end portions of the needle therebetween forming a plane 84 transverse to the axis of needle 78 which defines the tip of needle 78, and the apexes 86 of the curvilinear shaped openings 82 extending toward housing 12.

In the preferred embodiments of the present invention, sleeve 22 extends toward the plurality of spaced apart openings 58, 64, 72 and 82 with its open end 56 terminating short of the plurality of the spaced apart openings, i.e. terminating at a distance from housing 12 less than the distance from the housing to the plurality of spaced apart openings. It is also preferred in the embodiments of this invention that each of the plurality of spaced tip end apart openings defined by the needle extends axially from the operating end of the needle toward handpiece housing 12 a distance in the order of 0.1 inch. It is particularly preferred that the open end 56 of sleeve 22 terminate in the order of 0.1 inch from the side or apex of spaced apart openings 58, 64, 72 and 82 closest to end 56. In this manner, during operation of the probe, a substantial portion of fluid passing through irrigating fluid passage 42 and exiting open end 56 of annular space 54 between the needle and sleeve 22, reaches the operating end of the needle, and hence the surgical site; while another substantial portion of the fluid exiting open end 56 of annular space 56 passes through spaced apart tip end openings 58, 64, 72 and 82 and into bore 20 of the needle and suction passage 28 to ensure the continuous flow of fluid therethrough to improve aspiration of particles, even if the end of the needle is temporarily blocked.

Another embodiment of the present invention is shown in FIGS. 10 and 11, wherein sleeve 22 includes a tapered portion 88, which provides a greater field of vision of the operating end 30 of needle 18 during operation of the probe. This embodiment, i.e. providing a tapered portion 88 to the sleeve, is applicable to each of the embodiments shown and described herein, and further permits sleeve 22 to have a substantially cylindrical main portion between tapered portion 88 and the flared end portion 48 of the sleeve.

Experiments were performed using a probe construction in accordance with the embodiment shown in FIGS. 1-3 of the drawing. For comparison, an identical construction was also utilized, but using a needle having two opposed preaspiration holes instead of a needle constructed in accordance with the present invention. In the experiments the following needle constructions were employed:

| | |
|---|---|
| Needle A - | Length: 3.125 inches (from tip to shoulder abutting horn of handpiece) |
| | Two rectangular, axially aligned slots diametrically opposed, each 0.010 inch wide and 0.100 inch long (from end of needle) |
| | Distance of closed end of slots to open end of sleeve: 0.060 inch |
| Needle B - | Length: Same as in Needle A |
| | Two round holes diametrically opposed, each 0.013 inch in diameter, the centerline of each hole spaced .022 inch from end of needle |
| | Distance of centerline of holes to open end of sleeve: 0.020 inch |

EXPERIMENT I

Using an ULTRA 4300 Ultrasonic Aspirator, available from Sharplan Lasers, Inc., 1 Pearl Court, Allendale, N.J. 07401, Needle A and Needle B above were consecutively installed on the handpiece supplied therewith in accordance with instructions provided with the aspirator, followed by the installation of a standard handpiece sleeve about the needle and to the handpiece also in accordance with the instructions provided with the aspirator. The aspirator was energized with 100% vibration at the frequency and voltage indicated below, and with 50% irrigation and 50% suction (aspiration). The needles were applied to raw meat in both red (muscle) areas and white (ligament) areas for 2 minute intervals followed by 30 second rest intervals with the following results:

|                                      | Material removed (grams) |
|---|---|
| Needle A, at 22,410 kHz: | |
| 0:00–2:00 minutes | 4.9 |
| 2:30–4:30 minutes | 5.4 |
| 5:00–7:00 minutes | 3.8 |
| Needle A, at 22,440 kHz: | |
| 0:00–2:00 minutes | 5.7 |
| 2:30–4:30 minutes | 5.1 |
| 5:00–7:00 minutes | 3 |
| Needle A, at 22,529 kHz: | |
| 0:00–2:00 minutes | 6.3 |
| 2.30–4:30 minutes | 6.3 |
| 5:00–7:00 minutes | 3.4 |
| Needle B, at 22,510 kHz* | |
| 0:00–2:00 minutes | 1.2 |
| 2:30–4:30 minutes | 2.2 |
| 5:00–7:00 minutes | 4.5 |

*only red meat removed

In addition to the greater amount of material removed, Needle A in accordance with the present invention removed both red and white meat areas, representing muscle and ligament, while Needle B with pre-aspiration holes could only remove material from red meat areas, representing muscle only.

Further, experiments have shown preferred orientation for operating the handpiece in accordance with the present invention is to have spaced apart tip end openings oriented with their centerline forming a plane parallel to the ground (where two openings are present) rather than oriented with their centerlines forming a plane perpendicular to the ground. It has also been found preferable to move the needle across the material to be removed and hence the handpiece horizontally, that is along the plane formed by the spaced apart tip end openings oriented as preferred, as noted above, rather than in a vertical direction.

EXPERIMENT II

Using Needle A described in Experiment I under identical conditions of operation, the following amounts of material were removed:

| Needle A, the two openings with centerlines horizontally oriented and moved horizontally across material: | |
|---|---|
| 0:00–2:00 minutes | 6.2 |
| 2:30–4:30 minutes | 5.6 |
| 5:00–7:00 minutes | 5 |
| Needle A, the two openings with centerlines vertically oriented and moved horizontally across material: | |
| 0:00–2:00 minutes | 2.2 |
| 2:30–4:30 minutes | 4.4 |
| 5:00–7:00 minutes | 5.6 |

As is known to those skilled in the art, the length of the hollow operating needle should be selected to match the frequency of the vibrations transmitted from the ultrasonic motor, so that the needle will resonate at the desired frequency. For example, a needle with an effective length of 2.125 inches, that is from its tip end to its abutment with the horn, was found to resonate at 22.4 kHz.

While a particular embodiment of the needle and the ultrasonic probe of the invention has been shown and described, it will be appreciated by those skilled in the art that changes and modifications may be made thereto without departing from the invention in its broader aspects and as set forth in the following claims.

What is claimed is:

1. A hollow operating needle for an ultrasonic surgical probe handpiece and adapted to extend therefrom, the handpiece having an ultrasonic motor capable of generating ultrasonic vibrations contained therein, having means for connecting the handpiece and needle to a source of suction, having an open-ended sleeve generally concentrically positioned about the needle extending from said handpiece less than the distance that the operating needle extends from the handpiece, the sleeve defining an open-ended annular space with the needle, and having means for connecting the handpiece to a source of fluid such that fluid can flow through the annular space between the needle and the sleeve for exiting from the open end of the annular space defined by the sleeve, the hollow operating needle comprising:

a. an elongated, tapered body having one end thereof larger than the other and defining an elongated hollow bore extending from one end of the tapered body to the other, a portion of said body adjacent said larger end defining a larger end portion;

b. means on the larger end portion of said body for coupling the needle to the ultrasonic motor for receiving and transmitting ultrasonic vibrations from the motor along the length of the needle to the operating tip end;

c. said tapered, hollow body terminating in said operating tip end at its end opposite the larger end portion and defining an operating tip end portion; and d. said operating needle defining a plurality of spaced apart openings in the operating tip end portion thereof extending from said operating tip end portion toward said larger end portion a distance substantially less than the distance from said operating tip end portion to the larger end portion; whereby during operation of the probe a substantial portion of fluid passing through the annular space between said operating needle and the sleeve and exiting therefrom reaches the operating tip end of the needle and another substantial portion of the fluid passes through the plurality of openings defined in the operating tip end portion thereof for passage through the bore of the needle without reaching the operating tip end of the needle.

2. The hollow operating needle of claim 1, wherein said needle is dimensioned such that the plurality of spaced apart openings in said needle are positioned outside the open end of the sleeve.

3. The hollow operating needle of claim 1, wherein said needle defines a plurality of spaced apart rectangular openings in the operating tip end portion thereof extending coaxially from said operating tip end portion toward said larger end portion a distance substantially less than the distance from said operating end portion to the larger end portion, with the longer sides of the rectangular openings defined in the needle being coaxial with the bore of the hollow body of the needle; whereby during operation of the probe a substantial portion of fluid passing through the annular space between said operating needle and the sleeve and exiting therefrom reaches the operating tip end of the needle and another substantial portion of the fluid passes through the said plurality of openings defined in the operating tip end portion thereof for passage through the bore of the needle without reaching the operating tip end of the needle.

4. The hollow operating needle of claim 3, wherein said needle defines a pair of spaced apart rectangular openings in the operating tip end portion extending coaxially from said operating tip end portion toward said larger end portion, with the longer sides of the rectangular openings defined in the needle being coaxial with the bore of the hollow body of the needle.

5. The hollow operating needle of claim 3, wherein said operating needle defines three spaced apart rectangular openings extending co-axially from the operating end portion thereof toward the handpiece.

6. The hollow operating needle of claim 3, wherein said needle is dimensioned such that the plurality of spaced apart rectangular openings in said needle are positioned outside the open end of the sleeve.

7. The hollow operating needle of claim 1, wherein each of the plurality of spaced apart openings defined by the needle is triangular in shape, with the bases of said triangular openings forming an imaginary plane which is transverse to the bore of the elongated body, and which defines the operating tip end of the needle and, the apexes of the triangular openings extending toward the handpiece.

8. The hollow operating needle of claim 1, wherein each of the plurality of spaced apart openings defined by the needle extends toward the handpiece in curvilinear shape, with the bases of the openings forming an imaginary plane which is transverse to the bore of the elongated body, and which defines the tip end of the operating end of the needle, and with the apexes of the openings extending toward the handpiece.

9. The hollow operating needle of claim 8, wherein each of the plurality of spaced apart openings defined by the needle extends toward the handpiece in arcuate shape, with the bases of said openings forming an imaginary plane which is transverse to the bore of the elongated body, and which defines the tip end of the operating end of the needle, and with the apexes of the openings extending toward the handpiece.

10. The hollow operating needle of claim 1, wherein the portion of each of the openings defined in the needle closest to the larger end portion of the body, is arcuate with the apex of the arcuate portion being closest to the larger end portion of the needle.

11. The hollow operating needle of claim 10, wherein the plurality of openings defined by the needle is a pair of equidistantly spaced rectangular openings, with the portion of each opening defined in the needle closest to the larger end portion of the body being arcuate.

12. An ultrasonic surgical probe comprising:

a handpiece having an ultrasonic motor contained therein, said motor being capable of generating ultrasonic vibrations;

a hollow operating needle extending outwardly from said handpiece to an operating tip end thereof and coupled to said motor for receiving and transmitting ultrasonic vibrations therefrom along the length of said needle to said operating end;

said handpiece having means for connecting said hollow operating needle to a source of suction such that suction can be applied to cause material to be drawn into the end of said operating needle and to pass therethrough;

said operating needle defining a plurality of spaced apart openings extending from the operating tip end portion thereof toward said handpiece a distance of less than the distance from said operating tip end portion of the needle to the handpiece;

a sleeve generally concentrically positioned about said operating needle and extending from said handpiece toward but less than the distance that the needle extends from the handpiece to the plurality of spaced apart openings in said needle and terminating in an open end, said sleeve defining an open ended annular space with said needle; and said handpiece having means for connecting the handpiece to a source of fluid such that fluid can flow through the annular space between said operating needle and said sleeve for exiting from the open end of the annular space, whereby during operation of the probe a substantial portion of fluid passing through the annular space between said operating needle and said sleeve and exiting therefrom reaches the operating tip end of the needle and another substantial portion of the fluid passes through the plurality of openings defined in the needle for passage therethrough without reaching the operating tip end of the needle.

13. An ultrasonic surgical probe comprising:

a handpiece having an ultrasonic motor contained therein, said motor being capable of generating ultrasonic vibrations;

a hollow operating needle extending outwardly from said handpiece to an operating tip end thereof and coupled to said motor for receiving and transmitting ultrasonic vibrations therefrom along the length of said needle to said operating end;

said handpiece having means for connecting said hollow operating needle to a source of suction such that suction can be applied to cause fluid and solid material to be drawn into the end of said operating needle and to pass therethrough;

said operating needle defining a plurality of spaced apart substantially rectangular openings extending from the operating tip end portion thereof toward said handpiece a distance of substantially less than the distance from said operating tip end portion of the needle to the handpiece;

a sleeve extending from said handpiece and generally concentrically positioned about said operating needle, said sleeve terminating in an open end defining with said needle an open ended annular space, and said sleeve extending from the handpiece a distance less than the distance that the needle extends from the handpiece to the plurality of the spaced apart openings defined in the needle;

said handpiece having means for connecting the handpiece to a source of fluid such that fluid can flow through the annular space between said operating needle and said sleeve for exiting from the open end of the annular space, whereby during operation of the probe a substantial portion of fluid passing through the annular space between said operating needle and said sleeve and exiting therefrom reaches the operating tip end of the needle and a less than substantial portion of the fluid passes through the plurality of openings defined in the needle for passage therethrough without reaching the operating tip end of the needle.

\* \* \* \* \*